(12) United States Patent
Parrott

(10) Patent No.: US 6,489,135 B1
(45) Date of Patent: Dec. 3, 2002

(54) DETERMINATION OF BIOLOGICAL CHARACTERISTICS OF EMBRYOS FERTILIZED IN VITRO BY ASSAYING FOR BIOACTIVE LIPIDS IN CULTURE MEDIA

(75) Inventor: Jeff A. Parrott, Irvine, CA (US)

(73) Assignee: AtairginTechnologies, Inc., Irvine, CA (US)

( * ) Notice: Subject to any disclaimer, the term of this patent is extended or adjusted under 35 U.S.C. 154(b) by 15 days.

(21) Appl. No.: 09/837,308

(22) Filed: Apr. 17, 2001

(51) Int. Cl.[7] .............................. C12Q 1/42; C12Q 1/44; G01N 33/53

(52) U.S. Cl. ............................ 435/21; 435/19; 435/25; 435/26; 435/975

(58) Field of Search ............................ 435/21, 19, 25, 435/26, 975

(56) References Cited

U.S. PATENT DOCUMENTS 5,160,312 A * 11/1992 Voelkel ........................ 600/34

OTHER PUBLICATIONS

Ammit, A.J. et al., "The role of albumin in the release of platelet–activating factor by mouse preimplantation embryos in vitro," J. Reprod. Fert. (1997) 109, 309–318.

Barnett, Deborah K. et al., "What is the Relationship Between the Metabolism of Preimplantation Embryos and Their Developmental Competence?," Molecular Reproduction and Development, 43:105–133 (1996).

Battye, K.M. et al., "Production of platelet–activating factor by the pre–implantation sheep embryo," J. Reprod. Fert. (1991) 93, 507–514.

Chen, Jia–hua et al., "Production and Application of LPA Polyclonal Antibody," Bioorg. Med. Chem. Lett. 10 (2000) 1691–1693.

De los Santos, Maria Jose et al., "Role of Endometrial Factors in Regulating Secretion of Components of the Immunoreactive Human Embryonic Interleukin–1 System during Embryonic Development," Biol. of Reprod. 54, 563–574 (1996.

Frenkel, Rene A. et al., "The Biochemical Role of Platelet–Activating Factor in Reproduction," Prog. Lipid. Res. vol. 35, No. 2, pp. 155–168, 1996.

Kane, M.T. "Control Growth in Preimplantation Embryos," IJMS, Jan. 1991.

Khidir, Mohammed A. et al., "Rapid Inhibition of mRNA Synthesis during Preimplantation Embryo Development: Vital Permeabilization by Sysolecithin Potentiates the Action of α–Amanitin," Experim. Cell. Res. 219, 619–625 (1995).

Lash, G.E. et al., "Induction of early pregnancy factor activity in vitro by platelet–activating factor in mice," J. Reprod. Fert. (1997) 109; 187–191.

Minhas, Brijinder S. et al., "Effects of platelet activating factor on mouse oocyte fertilzation in vitro," Am. J. Obstet Gynecol. Dec. 19891714–1717.

Minhas, B.S. et al., "Platelet Activating Factor and Conception." Am. J. of Reprod. Immun. vol. 35, 1996, 267–271.

Morin, C. et al., "Possible implication of lysophosphatidylcholine in cell fusion accompanying implantation in rabbits," J. Reprod. Fert. (1992) 96, 827–836.

O'Neill, C. "Autocrine Mediators Are Required to Act on the Embryo by the 2–Cell Stage to Promote Normal Development and Survival of Mouse Preimplantation Embryos In Vitro," Biol. Reprod. 58, 1303–1309, (1998).

O'Neill, Chris "Embryo–derived Platelet Activating Factor," Reprod. Fertil. Dev. 1992, 4, 283–288.

O'Neill, C. "Evidence for the Requirement of Autocrine Growth Factors for Development of Mouse Preimplantation Embryos In Vitro," Biol. of Reprod. 56, 229–237 (1997).

O'Neill, Christopher, Ph.D. et al., "Use of a bioassay for embryo–derived platelet–activating factor as a means of assessing quality and pregnancy potential of human embryos," Fertility And Sterility, 47, 969–975, Jun. 1987.

Pike, I.L. "Comparative studies of embryo metabolism in early pregnancy," J. Reprod. Fert. Suppl. 29 (1981) 203–213.

Rappolee, Daniel A. "It's Not Just Baby's Babble/Babel: Recent Progress in Understanding the Language of Early Mammalian Development: A Minireview," Mol. Reprod Devel. 52: 324–240 (1999).

Riffo, Marta S. et al., "Role of Phospholipase $A_2$ in Mammalian Sperm–Egg Fusion: Development of Hamster Oolemma Fusibility by Lysophosphatidylcholine," J. of Experim.. Zoology 279: 81–88 (1997).

Riffo, Marta S. et al., "Study of the Acrosome Reaction and the Fertilizing Ability of Hamster Epididymal Cauda Spermatozoa Treated with Antibodies Against Phospholipase $A_2$ and/or Lysophosphatidylcholine," J. of Experim. Zoology 275: 459–468 (1996).

Ripps, B.A. et al., "Platelet–Activating Factor Production From in Vitro and In Vivo Fertilized Murine Embryos is Similar," AJRI 1993: 30: 101–104.

Rout, Ujjwal K. et al., "Ethanol–induced intracellular calcium mobilization rapidly alters gene expression in the mouse blastocyst," Cell Calcium (1997) 22(6), 463–474.

(List continued on next page.)

Primary Examiner—Louise N. Leary
(74) Attorney, Agent, or Firm—Orrick, Herrington & Sutcliffe LLP

(57) ABSTRACT

The present invention provides methods for determining various biological characteristics of in vitro fertilized embryos, including overall embryo health, implantability, and increased likelihood of developing successfully to term. More specifically, the present invention concerns analyzing media specimens of in vitro fertilization cultures for levels of bioactive lipids in order to determine these characteristics.

45 Claims, No Drawings

OTHER PUBLICATIONS

Ryan, John P. et al., "Platelet Activating Factor (PAF) Production by Mouse Embryos In Vitro and Its Effect on Embryonic Metabolism," J. of Cell Biochem. 40: 387–395 (1989).

Simón, Carlos et al., "Coculture of Human Embryos With Autologous Human Endometrial Epithelial Cells in Patients with Implantation Failure," J. of Clin. Endocrin. & Metabol. 84, 2638–2646 (1999).

Smal, M.A. et al., "Examination for platelet–activating factor production by preimplantation mouse embryos using a specific radioimmunoassay," J. Reprod. Fert. (1990) 90, 419–425.

Suzuki, Hiroto et al., "Evidence for the Production of Platelet–Activating Factor by Murine Embryos and Its Putative Role in the Maternal Physiology," Biochem and Molecular Biol. Int'l, 37: 617–626 (Nov. 1995).

van der Weiden, R.M.F. et al., "Influence of prostaglandins and platelet activating factor on implantation," Human Reprod. 6:436–442 (1991).

\* cited by examiner

DETERMINATION OF BIOLOGICAL CHARACTERISTICS OF EMBRYOS FERTILIZED IN VITRO BY ASSAYING FOR BIOACTIVE LIPIDS IN CULTURE MEDIA

FIELD OF INVENTION

The present invention enables the determination of various biological characteristics of in vitro fertilized embryos, including overall embryo health, implantability, viability, and likelihood of successful development to term. More specifically, the present invention concerns analyzing media specimens of in vitro fertilization cultures for levels of bioactive lipids in order to determine the optional characteristics for media formulation to increase embryo viability and reduce the frequency of multiple births.

BACKGROUND

As many as 30% of couples attempting to conceive suffer from infertility. Due in part to the increasing age of pregnancy, infertility is on the rise. For men, infertility is usually caused by low sperm count or poor motility. For women, common causes include oviduct occlusion, abnormal ovulation cycles, and inhospitable vaginal mucus. Treatment options are available, depending on the source of the problem. However, even with treatment, many couples are not able to conceive in the traditional fashion.

In vitro fertilization (IVF) has been used increasingly to assist infertile couples in becoming pregnant. IVF generally includes the steps of: recovery of mature eggs from the female patient or a donor; incubation of the eggs in culture media; collection of sperm from the male patient or a donor; culture and preparation of the sperm for addition to the egg culture media (including capacitation procedures); fertilization of the eggs by the sperm; monitoring the embryos during early embryogenesis; and, finally, transfer of fertilized oocyte into the uterine cavity.

To harvest the oocytes, gonadotropin is administered to the ovaries of the donor to stimulate follicle growth and to increase the number of oocytes that mature in a single cycle. Just prior to ovulation, oocytes in the late stages of first meiotic division are aspirated from mature ovarian follicles. Generally, harvested oocytes are placed in a culture medium and fertilized by adding semen or cultured sperm. In some cases, sperm are micro-injected directly into the oocyte, bypassing the normal sperm/oocyte fusion process. After fertilization, the zygotes are microscopically monitored to the eight-cell stage, and further into blastocysts. Healthy embryos with normal phenotypic development and morphology are chosen for transfer by visual inspection. The embryos are then transferred directly into the uterine cavity through the cervical opening using a thin catheter.

Only about 20% of the couples utilizing IVF, however, carry an infant successfully to term. To increase the chances for a successful pregnancy, three or four embryos are usually transferred at the same time. Although a single pregnancy is desired, multiple pregnancies often result. Multiple pregnancies pose health risks for the mother during pregnancy, and can cause emotional and economic problems in family planning. The alternative of terminating one of the pregnancies poses a difficult ethical and emotional dilemma for many couples, and successful delivery of the remaining fetus cannot be ensured. Therefore, there is a need for the ability to select single embryos which are likely to develop successfully upon transfer into the uterus. Similarly, there is a need for the ability to de-select embryos that are unlikely to survive to term. As an embryo's probability of survival generally decreases with culture time, a need also exists for the ability to rapidly assess embryo health as early as possible after fertilization.

In recent years, platelet activating factor (PAF) has been discussed as a possible indicator of embryo viability. PAF (1-alkyl-2-acetoyl-sn-glycero-phosphocholine) seems to be involved in an autocrine hormonal signaling pathway in early embryogenesis. PAF also seems to be involved in paracrine pathway between the mother and the child, and has been detected in the culture medium of embryos that develop successfully to term. However, hormonal signaling in the early stages of development is complex, and a multitude of pathways and signaling mechanisms are involved in embryogenesis. PAF alone has not proven a sufficient indicator of embryo viability, and the role of small hormone molecules both in indicating and maintaining embryo health is not well understood. There is no current adequate molecular marker, or combination of markers, which indicates proper embryonic development at the very early stages of life. The structural formula for PAF is shown below (although the alkyl chain may be of varying lengths):

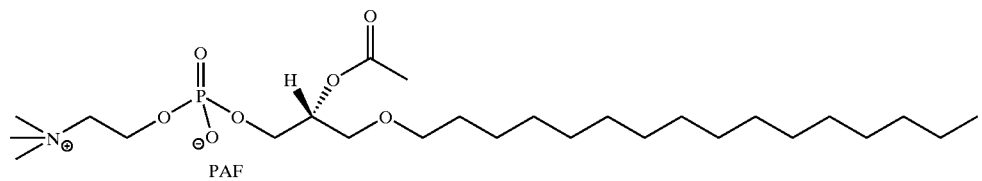

PAF

SUMMARY OF INVENTION

Thus, in a primary aspect, the present invention provides the ability to determine the implantability, overall viability, and likelihood of successful development of an embryo fertilized in vitro. The present invention comprises analyzing the presence or concentration of one or more bioactive lipids in culture media specimens obtained from IVF cultures containing the embryo. Differences in levels of specific types of bioactive lipids in an IVF culture sample specimen where the bioactive lipid concentrations deviate significantly from the levels of bioactive lipids found in culture specimens from embryos which successfully developed to term, those deviations reveal differences in the biochemical environment in which the embryo develops and are indicative of a difference in probability that the embryo will implant or develop normally to term. The present invention contemplates analyzing bioactive lipids from either single or multiple embryo cultures in media, as well as co-cultures of single or multiple embryos grown on a bed of feeder cells and using this analysis to make informed choices about the likelihood of successful fertilization and full-term development.

Specifically, the invention contemplates measuring the presence or concentration of bioactive lipids, comparing these concentrations to a normal, pre-existing, or established values for the specific embryo or media, and correlating these differences to the underlying biochemical status of the embryo, including the probability that the embryo will accede through viability to normal development, or will result in a multiple-birth pregnancy. Also, The ability to analyze the underlying biochemical status of the embryo provides the ability to analyze the chemical composition of the media and the ability to alter the chemical composition of the media through supplementation with chemical or biochemical agents to affect the viability of the embryo or the probability of a multiple-birth pregnancy. By analyzing one or more lipids, a multi-component lipid profile can be constructed for the culture media such that the lipid profile of the culture media can be correlated to viability, or, where appropriate, the composition of the culture media may be changed according to the concentration of one lipid or the multi-lipid profile. Moreover, an individual embryo, or group of embryos, can be monitored over time to determine how the lipid profile and the culture media is altered through natural development or through chemical or biochemical intervention to titrate the composition of the culture media to reach a desired level indicative of viability or the avoidance of multiple pregnancies. Therefore, the invention enables both the selection of healthy embryos and the deselection of unhealthy embryos to increase the probability of success of in vitro fertilization procedures. The ability to transfer a single healthy embryo with an increased probability of success, instead of several embryos with unknown probabilities of success, will result in fewer undesired multiple birth events.

Suitable bioactive lipids for analysis in the present invention include lysophospholipids, phospholipids, sphingolipids, and combinations and subspecies thereof. In addition to analyses of bioactive lipid species, precursors and metabolites of these bioactive lipids, such as glycerophosphatidyl compounds, may also be analyzed in the method as indicators of embryo health and viability. Various analytical methods of measuring the levels of bioactive lipids in the embryo culture media are contemplated in the present invention. In a preferred embodiment, enzymatic assays are used to measure levels of bioactive lipids in the sample embryo culture media. Generally, in enzymatic methods, lysophospholipids or glycerophosphatidyl compounds in the specimen are selectively converted into glycero-3-phosphate, and measured by a redox coupling reaction with NADH or NADPH. In an alternative embodiment, liquid chromatography-mass spectrometry is used to detect and measure the bioactive lipids present in the culture media sample. In another alternative embodiment, antibodies specific for particular bioactive lipid species or derivatives may be utilized in an immunoassay for the bioactive lipids.

In another aspect, the present invention also provides pre-packaged diagnostic kits for determining embryo biological characteristics by measuring certain bioactive lipids in an embryo culture media specimen. In preferred embodiments, these kits contain enzymes and reagents necessary to assay the sample for bioactive lipid concentrations, as well as standards and instructions for determining whether the assayed level is indicative of an increased or decreased probability for successful development of the embryo.

DETAILED DESCRIPTION

As discussed above, the ability to identify an embryo that is likely to implant properly in the uterine cavity and to develop normally to term is of great importance to the in vitro fertilization process. By eliminating the necessity to transfer multiple embryos for implantation, the overall success rate of the in vitro fertilization process may be enhanced, avoiding undesired multiple pregnancies. The present invention provides a method for determining the biological characteristics of embryos, including implantability and likelihood of normal development, by analyzing sample media from IVF embryo cultures at the very early stages of embryo development in order to determine which embryos are likely to develop successfully after transfer into a patient.

In the present invention, bioactive lipids, their precursors, and their metabolites in a sample media are analyzed to determine the viability of the embryo, preferably based on predetermined values or a lipid profile for the media, a measured value for the media, or a titrated value based on a series of measurements of bioactive lipids in the media. Small amounts of bioactive lipids in IVF cultures may be assayed accurately and reliably by biochemical means or mass spectrometry. Bioactive lipids analyzed in the present invention comprise one or more lipids selected from the lysophospholipid (LPX) and sphingolipid families. As used herein, the term bioactive lipids also encompasses precursors or metabolites of those lipids, such as glycerophosphitidyl (GPX) compounds, although they are not technically lipids. Bioactive lipid precursors may be measured in the methods of the invention.

LPX species for analysis pursuant to the invention include, among others, lysophosphatidic acid (LPA), lysophosphatidyl choline (LPC), lysophosphatidyl serine (LPS), lysophosphatidyl ethanolamine (LPE), lysophosphatidyl inositol (LPI), and lysophosphatidyl glycerol (LPG). Lysophospholipids have the general structure of a glycerol backbone with a phosphate or a derivatized phosphate such as choline, inositol, ethanolamine, glycerol, or serine at the sn-3 position; a single fatty acid chain located at the sn-1 or sn-2 position, linked to the glycerol backbone by an acyl linkage; and a hydroxyl at the unoccupied sn-1 or sn-2 position. Alternatively, an long-chain alcohol is linked to the glycerol backbone at the sn-1 or the sn-2 position by an alkyl or alkenyl linkage with a hydroxyl at the unoccupied sn-1 or sn-2 position. These compounds have the following general structures:

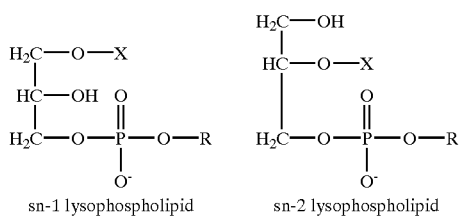

where X is any fatty acid, alkyl, or alkenyl chain. Such carbon chains include, but are not limited to 18:0, 16:0, 18:1, 18:2, 20:4n-6 and 22:6n-3, attached through an acyl (G—O—COOR1), alkyl (G—O—CH2—R1) or alkenyl bond (G—O—CH=R1),

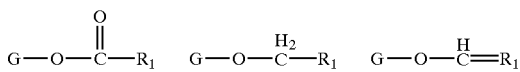

where "G" is the glycerol backbone. X may include such fatty acids as palmitic, palmitoleic, stearic, oleic, linoleic, arachidonic, and docasahexahoic fatty acid linked. R can be any phosphate derivative moiety, including, but not limited to, hydrogen, choline, inositol, ethanolamine, glycerol, and serine. More generally, the lysophospholipids may be represented by the structural formula:

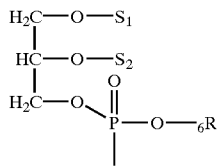

(5)

wherein $S_1$ is either X (as defined above) or hydrogen; $S_2$ is hydrogen if $S_1$ is X, or X if $S_1$ is hydrogen; and R is as defined above. Common lysophospholipids for detection using the invention method include, but are not limited to, LPA, LPC, LPS, LPE, LPI, and LPG, and their specific fatty acid/alcohol side chain forms.

Sphingolipids contemplated for analysis in the present invention comprise, among others, sphinganine-1-phosphate, sphingosine-1-phosphate (S1P), sphingosylphosphorylcholine (SPC), and sphingomyelin. The structural formulae for these sphingosyl compounds are shown below:

Sphingosine-1-Phosphate:

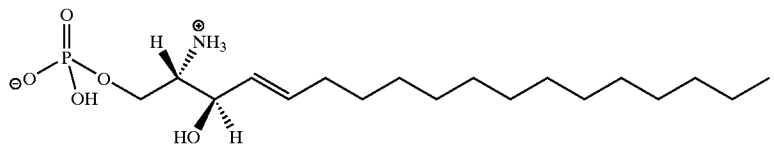

Sphinganine-1-Phosphate:

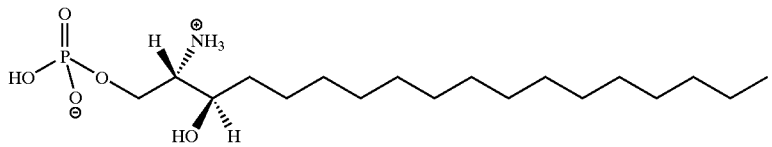

Sphingomyelin:

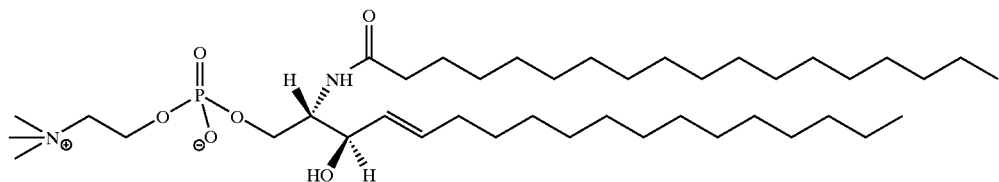

Sphingosine-phosphorylcholine (SPC):

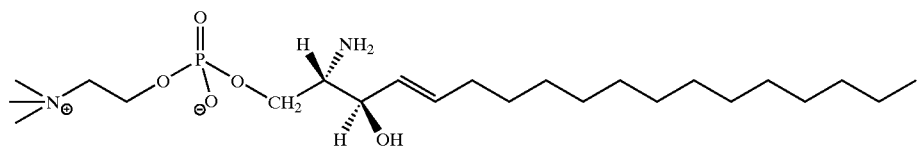

Thus, sphingosyl compounds, which are the sphingomyelin analogs of lysophospholipids, have the basic structural formula:

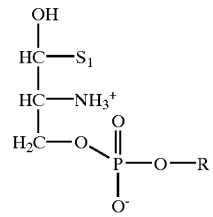

wherein $S_1$ is any alkyl or alkenyl of 15 carbons, and wherein R is any phosphate derivative moiety, including, but not limited to, hydrogen, choline, inositol, ethanolamine, glycerol, and serine. Thus, in addition to the derivative SPC, sphingosylphosphorylinositol (SPI), sphingosylphosphorylethanolarnine (SPE), sphingosylphosphorylglycerol (SPG), and sphingosylphosphorylserine (SPS) are also suitable bioactive lipid analytes for measurement in the methods of the present invention. By convention, 1-unsaturated $S_1$ sphingosyl compounds are called "sphingosine"

compounds, and saturated $S_1$ sphingosyl compounds are called "sphinganine" compounds.

In addition to the bioactive lipids described above, precursors and metabolites of bioactive lipids may also be assayed. Precursors include, among others, one or more of phospholipids (2 fatty acid chains), glycerophosphatidyl compounds (GPX), monoglyceride (MG), and digycleride (DG). Metabolites comprise, among others, one or more of glycerophospholipids (GPX), and monoglyceride (MG). Glycerophosphatidyl compounds (GPX) suitable for assaying in the methods of the present invention comprise, among others, glycerol-3-phosphate (G3P), glycerophosphatidyl inositol (GPI), glycerophosphatidyl choline (GPC), glycerophosphatidyl serine (GPS), glycerophosphatidyl glycerol (GPG), and glycerophosphatidyl ethanolamine (GPE). These compounds are metabolically related to lysophospholipids, and have the basic structure above, wherein both $S_1$ and $S_2$ are hydrogen. In addition, bioactive lipid "R" groups may be measured, such as choline, serine, ethanolamine, inositol, glycerol, and phosphate derivatives of these groups. GPX, MG, DG, and the derivative groups may constitute either a precursor or a metabolite. Additional precursors and metabolites not specifically mentioned herein are well known to one of ordinary skill in the art.

To ascertain standard levels of bioactive lipids which are indicative of a desirable biological characteristic, such as viability, media specimens from successful IVF embryo cultures are analyzed for the levels of bioactive lipids present. "Successful" IVF embryos will be defined by the desirable biological characteristic to be measured, including implantation success rate, viability of the embryo in the uterus, length of development to term, successful development to term, and avoidance of multiple pregnancies. Media specimens from unsuccessful cultures may also be analyzed for comparison and validation of the standard level. By comparing the levels of bioactive lipids in the culture media of successful and unsuccessful embryos, one of ordinary skill in the art is able to determine levels of bioactive lipids which are indicative of viability, implantability, and an increased likelihood of development to term.

In general, a standard level or profile of bioactive lipids is developed from this data which correlates with the improved viability, implantability, and likelihood of developing to term for an embryo in IVF culture. Significant deviation from this standard level (meaning a deviation greater that seen in embryos which are successful) is indicative of a decreased extent of the desirable biological characteristic (i.e., a decreased probability of implantation, or a decreased probability of developing to term.) In preferred embodiments, this standard level may be determined empirically from a statistically significant population of successful embryo culture specimens, and expressed as a number with a standard deviation. The standard level may the mean or median level of the bioactive lipid for culture specimens from embryos which exhibit the desirable biological characteristic, or may be derived through some other statistically valid means. This approach will be useful where the detection mechanism is sufficiently accurate to yield reproducible quantitative results. In another embodiment, the standard level for comparison may be a sample of culture media which is spiked with bioactive lipids to the standard level, or a culture media specimen (or mixture of specimens) derived from successful embryos. Based on the foregoing information, the chemical formulation of the cultured media may be designed or altered to reach a specific profile of bioactive lipids to achieve the aims of the in vitro fertilization. Thus, the invention includes specially formulated in vitro fertilization media based on the analysis of preferred bioactive lipid concentrations. Once this data is possessed, the chemical composition of the media may be altered in respect of the combination of one or more bioactive lipids. For example, particular bioactive lipids may be added to supplement the concentration in the media, or chemical agents may be introduced to remove or inactivate elevated levels of undesirable bioactive lipids. When the bioactive lipid profile is monitored over time, the individual concentrations of various lipids can be supplemented or altered as desired.

To determine viability of an embryo in question, a media specimen is collected from the IVF embryo culture, and then analyzed to determine the level of one or more bioactive lipids, precursors, or metabolites present in the specimen. Preferably, the level of the analyte is compared to a control media sample which has not been incubated with an embryo. Utilizing media controls can assist in correcting for natural variations in media compositions which may occur in culture media which are not wholly defined. By comparing the types of bioactive lipids and their concentrations to the standard levels, a determination is able to be made as to the likelihood of whether the embryo will implant and develop successfully to term. In the embodiments of the present invention, the level of a single bioactive lipid may be detected, or two or more bioactive lipids may be detected.

In alternative embodiments, multiple IVF culture specimens may be collected over a time interval, and the change in bioactive lipid levels over the course of the time interval determined. This is compared to a standard change in the level of the bioactive lipids assayed, obtained in a manner similar to that described above for the standard level, wherein multiple samples are collected from the IVF embryo cultures over a similar time interval. Similar to the analysis above, a significant deviation in the change observed in the test culture specimen, as compared to the standard change, would indicate a decreased extent of the desirable biological characteristic. Thus, the invention analyzes one or more bioactive lipids, correlates that measurement to a standard that has been predetermined or is determined according to the practice of the invention, and then determines a biological characteristic of the embryo, such as viability, probability of a certain term length or full term of the chance of a multiple pregnancy. Based on a determination of the selected characteristic, a decision is made whether to use the embryo or select an embryo with more desirable characteristics based on the analysis of the media described herein.

The determination of the desirable biological characteristic may be expressed in terms of a "bright line test" or a probability or other gradient measure. For example, in a bright line test, if a specific bioactive lipid is present at a zero or undetectable level in the media specimen, or below a definite threshold, the embryo is deemed not likely to survive, whereas if the bioactive lipid is present at detectable levels or above a certain threshold, the embryo is deemed likely to survive. Alternatively, the determination may be expressed as an embryo's likelihood or percentage of success. For example, where the analysis involves three bioactive lipids, detecting all three lipids at the standard level would give the strongest indication (i.e., 90% chance) of likelihood of success followed by detecting only two lipids (i.e., 60% chance). Detecting only one of the three lipids would indicate a lower chance of success (i.e., 30% chance). As will be appreciated by those of skill in the art, the analysis or measurement of the bioactive lipids can be conducted by determining an increase or decrease from a pre-existing standard, an increase or decrease from a previous measurement, or an absolute value relative to zero or a standard threshold or variable concentration established through testing or experience.

Various types of in vitro fertilization culture media may be used. To insure that the standard level is correct for any particular culture media type, it is preferred that a standard level be determined empirically for any type of culture media assayed. Moreover, because the chemical composition of various culture media may differ depending on the manufacturer or the specific formulation used by an in vitro fertilization clinic or facility, it may be necessary to determine an individual lipid profile or series of profiles for each type of media or each specific formulation used. Because this analysis necessarily involves a variation of multiple factors, although it is preferred that samples come from a single-embryo culture, which will provide information about that specific embryo, multiple embryo culture specimens may also be assayed utilizing the invention. The information generated from these tests is limited, however, to determinations regarding the embryos as a population, and the bioactive lipids characteristics of one embryo may mask those of another.

IVF culture media specimens include those derived from cultures where the fertilized ovum is cultured alone (as the only cell) in IVF media o for use with co-culture systems, wherein embryos are fertilized and allowed to develop on a bed of feeder cells. The feeder cells are thought to interact and communicate with the embryo in biochemical pathways to facilitate growth and development. Active communication between the feeder cells and the embryo may include important bioactive lipids in paracrine communication pathways. In some IVF culture systems, reproductive tissues such as oviduct cells and endometrial cells are used to produce feeder cell lines. In a more preferred practices, human cell lines are used as feeder cell lines, sometimes derived from the patient receiving the IVF embryo. This reduces the chances that an immunological response will develop upon transfer of the embryo. Further, multiple cell lines may be established from a single donor, and a most suitable cell line may be chosen for use in a co-culture system. In another aspect of the present invention, cell lines derived form a patient for use as feeder cells may be analyzed for the production of one or more bioactive lipids in order to choose the most suitable cell line. Essential bioactive lipids may indicate that a cell line is suitable for co-culturing. In contrast, cell lines that lack essential bioactive lipids may be deemed unfit for use as feeder cells.

In analyzing the media specimen, various sample sizes may be used. A suitable amount of culture media collected for sampling ranges preferably from approximately 1 to approximately 100 $\mu$l. Generally, no more than approximately 50 $\mu$l is needed for sampling. For the analytical assays described below, a preferred specimen volume ranges from approximately 1 to approximately 50 $\mu$l, more preferably from approximately 2 to approximately 10 $\mu$l, and most preferably approximately 5 $\mu$l. The present invention is advantageous in that only a small amount of sample specimen is required for an accurate analysis.

In normal IVF culture practices, the culture media is changed approximately two or three days after fertilization. The supernatant is decanted and fresh medium is added. In a preferred embodiment, the decanted media is used advantageously for the IVF culture specimen. The culture media, however, may be collected anytime during IVF. Preferably, the media specimen is collected when the embryo is between one hour to twenty days old, more preferably between one day and ten days old, and more preferably between two and five days old. For embodiments where the change of the detected bioactive lipid is assayed, two or more samples may be collected over a time interval within any of the above periods. Preferably, samples are collected over 1–5 days, more preferably over 1–3 days, and most preferably over 1 day or over 2 days. A small volume of media specimen (10–50 $\mu$l) may be carefully extracted without disrupting development of the embryo.

Several analytical techniques may be used for detecting and measuring bioactive lipids, including mass spectroscopy procedures and enzymatic methods to detect or quantitatively measure bioactive lipids in a sample specimen. In one embodiment of the methods of the invention, liquid chromatography and mass spectroscopy (LC-MS) is used to analyze sample specimen for bioactive lipids. Conditioned media samples from cultured embryos are diluted in a suitable solvent (e.g., 1:5 dilution in methanol) and centrifuged to remove any precipitate. In some embodiments, proteln-lipid interactions may be disrupted by adding acid, or other substances, to the sample. The samples are separated on an LC or high pressure (HP) LC column, and the individual bioactive lipids detected and quantified by mass spectroscopy. In a preferred embodiment, electrospray (ESI) MS or atmospheric pressure chemical ionization (APCI) MS is used. The mass spectroscopy technique is very flexible, and may be used to measure lysophospholipids, sphingolipids, and glycerophosphatidyl compounds, as well as to distinguish between various fatty acid or long-chain alcohol side chains and phosphatidyl substituents within the general species.

In a preferred embodiment, the bioactive lipids are assayed enzymatically. The enzymatic assay measures the total concentration of lysophospholipids or glycerophosphatidyl compounds present in a sample, and may also be used to measure the concentrations of specific bioactive lipids. The enzymatic assay preferably measures total GPX and/or LPX in the IVF culture specimen. Preferred embodiments for determining levels of LPX, LPA, and LPC in sample specimen are discussed in detail below. The specification of U.S. application Ser. No. 09/314,780, ENZYME METHOD FOR DETECTING LYSOPHOSPHOLIPIDS AND PHOSPHOLIPIDS AND FOR DETECTING AND CORRELATING CONDITIONS ASSOCIATED WITH ALTERED LEVELS OF LYSOPHOSPHOLIPIDS, filed May 15, 1999, and PCT Publication No. WO 00/23612, which is instructive for teaching methods of measuring LPX, LPA and LPC levels:, are fully incorporated herein by reference. In addition, the specification of U.S. application Ser. No. 09/558,880, METHOD OF DETECTING CARCINOMAS, filed Apr. 26, 2000, which is instructive for teaching methods of measuring GPX, G3P, and GPC levels, is also fully incorporated herein by reference.

A preferred method for enzymatically measuring bioactive lipids comprises measuring GPX and LPX in the specimen. The analytic method generally comprises converting GPX or LPX into G3P and assaying for the concentration of G3P produced in the sample. To convert LPX into G3P, lysophospholipase is used in the enzymatic reaction to cleave the fatty acid group from the G3P and other glycerophosphatidyl compound (GPX) backbones. GPX is preferably digested using glycerophosphatidyl compound phosphodiesterase (GPX-PDE) to cleave the substituent from the phosphate of the G3P backbone. Thus, the amount of G3P produced by both of these enzymatic cleavage reactions is directly proportional to the total amount of LPX in the media specimen. Similarly, to determine the amount of GPX in a sample, only the glycerophosphatidyl compound phosphodiesterase is used to cleave the phosphatidyl substituents from the GPX species.

The amount of G3P in the cleaved and uncleaved portions of the sample specimen is then quantified using conventional or enzymatic techniques. If the size of the media specimen is 2 ml or less, a quantification technique capable of detecting picomole amounts of the glycero compound is used. Suitable conventional techniques for detecting picomole amounts include mass spectrometry.

Another preferred technique for determining the amount of G3P in the samples is an enzymatic cycling reaction. Specifically, an enzyme cycling reaction using glycerol-3-phosphate dehydrogenase (GDH), glycerol-3-phosphate oxidase (GPO) and NADH is used to accumulate $H_2O_2$ and NAD. In the reaction, G3P is converted into dihydroxyacetone phosphate (DAP) and $H_2O_2$ using GPO in the presence of oxygen and water. In the presence of DAP, G3P dehydrogenase converts dihydroxyacetone phosphate back to G3P and oxidizes NADH to NAD. Alternatively, depending on the sensitivity of the NADH or $H_2O_2$ detection, a non-cycling reaction may be used.

The disappearance of NADH is monitored spectrophotometrically preferably at $OD_{340}$. In alternative embodiments, $H_2O_2$ production may be measured by colorimetry, fluorometry, or by chemiluminescence. For the colorimetric assay, any of a number of chromogenic substrates, such as 4-aminoantipyrine (AAP), pyrogallol, 2-($2^1$-Azinobis (3-ethylbenzthiazoline-sulfonic acid)(ABTS) and $3,3^1,5,5^1$-tetramethylbenzidine) (TMB), may be used with a peroxidase to generate detectable signal (e.g., $OD_{505}$ for AAP). Numerical values are obtained from a standard curve consisting of known concentrations of G3P, and assays are preferably performed in duplicate with both positive and negative controls. The difference between the detectable signal (e.g., $OD_{340}$ or $OD_{505}$) before and after the enzyme cycling reaction is directly proportional to the amount of G3P present.

Additional bioactive lipids, such as glycerol-3-phosphate (G3P) and lysophosphatidic acid (LPA), may also be determined as above by first separating LPA and G3P from the total lysophospholipid in the sample. In a preferred embodiment for determining the concentration of LPA and G3P, G3P is measured after being liberated from LPA in the absence of GPX-PDE. In this embodiment, G3P is detected using the enzymatic cycling reaction described above, but the remaining GPX compounds other than G3P are not detected. LPA is first cleaved into glycerol-3-phosphate and fatty acid using phospholipase B or lysophospholipase. The level of G3P is then measured using G3P dehydrogenase and oxidase in the cycling reaction as described above.

Additional bioactive lipids, such as glycerophosphatidylcholine and lysophosphatidylcholine, may also be determined as above by first separating LPC and GPC from the total lysophospholipid in the sample. In a preferred embodiment for determining the concentration of LPC and GPC, choline is measured after being liberated from GPC and LPC. LPC is first cleaved into glycerophosphatidyl choline and fatty acid using phospholipase B or lysophospholipase. The level of LPC is then determined by liberating choline and glycero-3-phosphate (G3P) from glycerophosphorylcholine using glycerophosphorylcholine phosphodiesterase (GPC-PDE), followed by a calorimetric enzymatic determination of choline using choline oxidase, 4-aminoantipyrine (AAP), 3,5 Dichloro-2-hydroxybenzenesulfonic acid sodium salt (HDCBS) and peroxidase. Choline is preferably detected by oxidizing to $H_2O_2$ and betaine and using peroxidase to form quinoneimine dye. Alternatively, G3P is measured using G3P dehydrogenase and oxidase in the cycling reaction as described above.

In other embodiments of the invention, immunoassay techniques may be utilized to measure the levels of bioactive lipids in the IVF media specimen. Antibodies to various biological lipids suitable for analysis have been described in the literature. For example, Chen, et al., "Production and Application of LPA Polyclonal Antibody," *Bioorg. & Med. Chem. Letters* 10:1691–1693 (2000), describes the production and use of an antibody to LPA, utilizing colloidal gold as an antigen carrier. Similar antibodies may be raised to other lysophospholipid species and utilized in immunoassay formats (e.g., sandwich or competitive immunoassays.) In addition, antibodies to bioactive lipid precursors or metabolites have been reported. For example, Echelon Labs (Salt Lake City, Utah) offers an anti-phosphoinositol antibodies, and immunoassay kits for the detection of phosphoinositol species. One of ordinary skill in the art would be able to readily adapt these antibodies for analysis of bioactive lipids in media to determine embryo characteristics pursuant to the invention.

To optimize detection of lysophospholipids, inhibitors may be used to prevent degradation of the glycerophosphatidyl compounds and lysophospholipids in the sample. Such inhibitors include phosphodiesterase inhibitors such as IBMX (3-Isobutyl-1-methylxanthine, CalBiochem, La Jolla, Calif.); Ro-20-1724 (CalBiochem); Zaprinast (CalBiochem) and Pentoxifylline (CalBiochem); general protease inhibitors such as E-64 (trans-Epoxysuccinyl-L-leucylamido-(4-guanidino)butane, Sigma); leupeptin (Sigma); pepstatin A (Sigma); TPCK (N-tosyl-L-phenylalanine chloromethyl ketone, Sigma); PMSF (Phenylmethanesulfonyl fluoride, Sigma); benzamidine (Sigma) and 1, 10-phenanthroline (Sigma); organic solvents including chloroform and methanol; detergents such as SDS or Trident X100; proteases that would degrade phospholipases such as trypsin (Sigma) and thermostable protease (Boehringer Mannheim Biochemicals, Indianapolis, Ind.); and metal chelators such as EDTA (Ethylenediaminetetracetic acid, Sigma) and EGTA (Ethylene glycol-bis-(beta-aminoethyl ether), Sigma). In some embodiments, $MgCl_2$ and/or EDTA are included in the assay buffers to optimally determine levels of each analyte.

In a preferred embodiment, microtiter plates may be used for small volumes of samples and reagents. An ELISA reader may also be used to monitor and help automate the assay, and the reduced processing times may in turn reduce variability between results. Also, micro-scale automated assay equipment, such as the Immuno I system available from Bayer, the Access system available from Beckman Coulter, or the Dimension R-L HM system available from Dade Behring may be used.

The present invention also contemplates convenient prepackaged diagnostic kits for enzymatically detecting levels of bioactive lipids such as GPX, GPC, LPX and/or LPC in IVF culture media specimens. Preferably, these kits contain enzymes and reagents necessary for determining the level of GPX, GPC, LPX and/or LPC as described above, as well as instructions to correlate the bioactive lipid levels assayed using the kits to embryo characteristics as described herein. For example, diagnostic kits preferably include enzymes and buffers for the cleavage of GPX, GPC, LPX and LPC. Exemplary enzymes for inclusion in such kits are phospholipase B, lysophospholipase, glycerophosphitidyl compound phosphodiesterase, and glycerophosphatidylcholine phosphodiesterase. In addition, the kits of the present invention preferably include reagents for determining concentrations of G3P, including enzymatic reaction reagents such as glycerol-3-phosphase dehydrogenase, glycerol-3-phosphate oxidase, NADH and other ancillary agents such as buffering agents, colorimetric reagents for the detection of peroxide generation, and EDTA for inhibiting degradation of G3P.

Optionally, the kits may include reagents necessary to separate GPC or LPC from the other lysophospholipids in the sample. Also optionally, the kits of the present invention include reagents for measuring choline liberated from GPC or LPC in the specimen. Such reagents may include, for example, choline oxidase, peroxidase, 4-aminoantipyrine (AAP), 3,5 Dichloro-2-hydroxybenzenesulfonic acid sodium salt (HDCBS), and other ancillary agents such as buffering agents.

The kits of the invention also comprise containers and measuring apparatus for carrying out the appropriate measurements. The kits of the invention may also include standards for comparison, which are preferably IVF culture media spiked with the appropriate level of the assayed bioactive lipids, in order to assure that the clinician has properly performed the analysis described herein when using the kit. Less preferably, such standards may also be derived from successful embryo culture media. Variations of specific container and combination embodiments of the kits of the invention may readily be devised by those of ordinary skill in the art utilizing the guidance herein provided.

EXAMPLES

The following examples are offered to further illustrate the various aspects of the present invention, and are not meant to limit the invention in any fashion. Based on these examples, and the preceding discussion of the embodiments and uses of the invention, several variations of the invention will become apparent to one of ordinary skill in the art. Such self-evident alterations are also considered to be within the scope of the present invention. All referenced patents, articles, and publications mentioned in this specification are explicitly incorporated by reference in their entirety.

Example 1

Assay of Media Specimen from In vitro Fertilization Culture to Measure Total Lysophospholipid (LPX) and Total Glycerophosphatidyl Compounds (GPX) By a Redox-Coupled Enzymatic Reaction IVF embryo conditioned culture media specimens were obtained from freshly cultured human embryos. Embryos were cultured in a media blend, containing RPMI media (from Irvine Scientific, Santa Ana, Calif.) as a base, with supplemental factors added. A control sample of the media blend was also obtained for comparison. Embryos were cultured in 0.1 ml media under a drop of oil to prevent evaporation. Embryos were maintained at 37° C. in a humidified incubator. Media samples were collected by aspiration from individually cultured human IVF embryos at 72 hours of development. Additional media was added to the embryo culture if in vitro development were to be continued. The aspirated media specimen was either processed immediately or stored at −20° C. or below until processing.

Reagents

Lysophospholipase (LYPL) was purchased from Asahi Chemical (Tokyo, Japan). Glycerol-3-phosphate oxidase (GPO) was purchased from Toyobo (Osaka, Japan). Glycerophosphorylcholine phosphodiesterase (GPC-PDE or GPX-PDE) and 4-aminoantipyrine (AAP) were purchased from Sigma Chemical Co., St. Louis, Mo. Glycerol-3-phosphate dehydrogenase (GDH), peroxidase (POD) and beta-Nicotinamide-adenine dinucleotide (NADH) were purchased from Roche (Boehringer Mannheim, Indianapolis, Ill.). 3,5-Dichloro-2-hydroxybenzenesulfonic acid (HDCBS) was purchased from Biosynth (Naperville, Ill.). Amplex Red reagent (10-acetyl-3,7-dihydroxyphenoxazine) was purchased from Molecular Probes, Inc. (Eugene, Oreg.). RPMI media was from Irvine Scientific (Santa Ana, Calif.). All lipid or glycerophosphatidyl standards were purchased from Avanti Polar Lipids, Alabaster, Ala. or Sigma Chemical Co.

Enzyme Assay

Using a 96 well microtiter plate, 5 µl of each sample was aliquotted into pairs of wells. In some cases, samples were diluted 1:10 in 50 mM Tris, pH 8.0 prior to being assayed. To one well of each pair, the "LPX+GPX" well, 100 µl of LYPL (0.05 Units)/GPC-PDE (0.0125 Units) was added. 100 µl of GPC-PDE (0.0125 Units) was added to the other "background GPX" well. The wells were then incubated at 37° C. for 15 minutes. Glycerophosphatidyl compounds were produced as an intermediate by LYPL digestion of LPX. G3P and the phosphoryl substituents were then liberated from the glycerophosphatidyl compounds using GPX-PDE (called GPC-PDE). G3P levels in each well were then determined by enzymatic assay of the digested samples. 95 µL of cycling reaction enzyme mix containing 10 units of G3P oxidase (GPO), 4 units of G3P dehydrogenase (GDH), and 1.5 mM NADH in 50 mM Tris (pH 8.0) was added to each well, and incubated at 37° C. for 30 minutes. The G3P oxidase converts G3P to dihydroxyacetone phosphate and $H_2O_2$, and G3P dehydrogenase converts the dihydroxyacetone phosphate back into G3P. This reaction oxidizes NADH to NAD, and, as cycling continues, both $H_2O_2$ and NAD accumulate.

The total amount of G3P was determined by determining the accumulation of $H_2O_2$ fluorometrically by adding 50 µl of a solution containing 0.8 units horseradish peroxidase and 3.2 mM Amplex™ Red reagent (10-acetyl-3,7-dihydroxyphenoxazine) in 50 mM Tris 8.0 and measuring the fluorescence using 545 nm excitation and 590 nm emission. Optionally, the accumulation of $H_2O_2$ was also determined calorimetrically by adding 50 µl of a solution containing 0.5 units peroxidase, 0.5% HDCBS and 0.15% AAP in 50 mM Tris 8.0 to each well and recording the absorbance at 505 nm. Optionally, the total amount of G3P was determined by monitoring the oxidation of NADH (i.e. the reduction of absorbance at 340 nm after the cycling action compared to $A_{340}$ before cycling).

Numerical values of G3P concentrations were obtained from a standard curve constructed from known G3P amounts. A control culture media was included within each assay (i.e. each plate) that was measured at different dilutions. In some cases, this control media was used to correct for background variations between different experiments. When the colorimetric method was used, the plate was blanked at 505 nm prior to color development.

Using fluorometric detection, the dynamic range of detection was 0.01 to 10 µM G3P, and in some cases, the dynamic range extended up to 35 µM G3P. Therefore, all samples were diluted 1:10 prior to being assayed to conserve sample volume. 65 embryo media samples and 1 control sample were analyzed. The results are shown in Table 1 and 2. Values were obtained for LPX+GPX and GPX alone. The difference between these values was calculated as the apparent total LPX. Cultured media samples were generally lower in GPX than the control media. However, the amount of LPX varied among different cultured media samples. In some samples, values for LPX were higher than control media, and in others values for LPX were lower. Generally, the changes in GPX were −8 μM to −25 μM, and the changes in LPX were −11 μM to +10 μM. The average and median values were as follows. Average and median values, in μM, for the samples were 20.6 and 21.8 (for LPX+GPX), 8.7 and 8.3 (for GPX), and 11.8 and 11.5 (for LPX) compared to average values for the control media of 36.4 (for LPX+GPX), 24.8 (for GPX), and 11.6 (for LPX). Average and median values, in μM, for changes during culture from control were −15.8 and −14.6 (for LPX+GPX), −16.1 and −16.5 (for GPX), and 0.2 and −0.1 (for LPX).

TABLE 1

| Sample | μM LPX + GPX | +/−SD | μM GPX | +/−SD | Calculated μM LPX |
|---|---|---|---|---|---|
| Control | 36.4 | 0.3 | 24.8 | 1.0 | 11.6 |
| 502 | 18.0 | 0.7 | 12.0 | 0.6 | 5.9 |
| 503 | 14.3 | 0.6 | 7.5 | 0.1 | 6.7 |
| 504 | 22.0 | 1.4 | 12.4 | 0.2 | 9.6 |
| 505 | 17.2 | 0.3 | 9.6 | 0.0 | 7.6 |
| 506 | 18.5 | 0.2 | 11.0 | 0.6 | 7.4 |
| 507 | 15.8 | 0.1 | 8.8 | 0.2 | 6.9 |
| 508 | 16.6 | 0.0 | 9.6 | 0.2 | 7.1 |
| 509 | 15.8 | 0.1 | 8.7 | 0.1 | 7.1 |
| 510 | 25.8 | 0.1 | 8.3 | 0.1 | 17.5 |
| 511 | 23.5 | 0.2 | 8.7 | 0.0 | 14.8 |
| 512 | 29.2 | 0.8 | 9.6 | 0.1 | 19.6 |
| 513 | 25.6 | 0.5 | 8.3 | 0.2 | 17.3 |
| 514 | 24.2 | 0.8 | 8.3 | 0.1 | 15.8 |
| 515 | 28.7 | 0.7 | 8.5 | 0.0 | 20.i |
| 516 | 26.9 | 1.8 | 8.3 | 0.0 | 18.6 |
| 517 | 25.8 | 0.9 | 8.5 | 0.1 | 17.3 |
| 518 | 11.8 | 1.2 | 4.4 | 0.0 | 7.4 |
| 519 | 25.1 | 0.1 | 8.6 | 0.0 | 16.5 |
| 520 | 18.6 | 2.1 | 8.2 | 0.1 | 10.5 |
| 521 | 26.7 | 0.6 | 8.7 | 0.1 | 18.0 |
| 523 | 23.2 | 0.2 | 8.4 | 0.0 | 14.8 |
| 524 | 29.1 | 0.8 | 9.2 | 0.1 | 19.9 |
| 525 | 22.5 | 2.8 | 7.9 | 0.1 | 14.5 |
| 526 | 23.0 | 0.5 | 8.4 | 0.1 | 14.7 |
| 527 | 9.3 | 1.2 | 3.4 | 0.2 | 5.9 |
| 528 | 21.5 | 0.2 | 8.2 | 0.0 | 13.2 |
| 529 | 23.1 | 0.4 | 8.3 | 0.1 | 14.9 |
| 530 | 23.8 | 0.5 | 8.2 | 0.0 | 15.6 |
| 531 | 20.1 | 2.1 | 8.0 | 0.1 | 12.1 |
| 532 | 28.0 | 0.1 | 9.1 | 0.1 | 18.9 |
| 533 | 22.2 | 2.3 | 7.9 | 0.2 | 14.3 |
| 534 | 29.4 | 0.8 | 9.5 | 0.1 | 20.0 |
| 535 | 8.7 | 1.3 | 2.8 | 0.7 | 5.9 |
| 536 | 12.1 | 2.1 | 5.9 | 2.4 | 6.1 |
| 537 | 30.4 | 0.7 | 8.5 | 0.1 | 21.9 |
| 538 | 14.3 | 1.4 | 6.4 | 1.8 | 7.9 |
| 539 | 11.5 | 2.3 | 6.2 | 1.9 | 5.3 |
| 540 | 12.8 | 2.6 | 3.8 | 0.9 | 9.0 |
| 541 | 12.2 | 3.4 | 4.5 | 0.6 | 7.7 |
| 542 | 19.6 | 0.1 | 6.8 | 0.1 | 12.8 |
| 543 | 19.6 | 0.5 | 8.1 | 0.3 | 11.5 |
| 544 | 25.2 | 0.2 | 13.6 | 0.0 | 11.6 |
| 545 | 26.6 | 0.2 | 10.2 | 0.2 | 16.4 |
| 546 | 27.1 | 0.1 | 17.3 | 0.7 | 9.7 |
| 547 | 1.1 | 0.2 | 0.1 | 0.0 | 1.0 |
| 548 | 22.8 | 1.4 | 8.0 | 0.6 | 14.8 |
| 549 | 5.6 | 0.2 | 2.1 | 0.2 | 3.5 |
| 550 | 13.3 | 0.2 | 3.8 | 0.0 | 9.5 |
| 551 | 45.8 | 0.0 | 28.4 | 0.1 | 17.4 |
| 552 | 19.6 | 0.5 | 8.9 | 0.2 | 10.6 |
| 553 | 22.9 | 0.8 | 8.6 | 0.2 | 14.2 |
| 554 | 27.3 | 0.2 | 10.2 | 0.0 | 17.1 |
| 555 | 26.9 | 0.8 | 17.0 | 0.8 | 9.8 |
| 556 | 16.1 | 0.0 | 5.7 | 0.0 | 10.5 |
| 557 | 13.4 | 0.9 | 5.6 | 0.3 | 7.8 |
| 558 | 11.8 | 0.6 | 5.3 | 1.7 | 6.5 |
| 559 | 17.2 | 0.2 | 8.3 | 0.5 | 8.8 |
| 560 | 16.6 | 0.8 | 7.8 | 0.7 | 8.8 |
| 561 | 18.9 | 0.4 | 8.2 | 0.2 | 10.7 |
| 562 | 21.8 | 1.9 | 8.8 | 1.1 | 13.0 |
| 563 | 33.2 | 5.8 | 17.2 | 0.9 | 16.0 |
| 564 | 10.5 | 0.5 | 2.3 | 0.0 | 8.2 |
| 565 | 24.7 | 0.4 | 12.6 | 0.5 | 12.1 |
| 566 | 26.9 | 1.4 | 21.9 | 0.3 | 5.0 |
| 567 | 15.3 | 2.0 | 8.4 | 0.8 | 6.9 |
| | LPX + GPX | +/−SD | GPX | +/−SD | LPX | +/−SD |
| Average | 20.6 | 7.4 | 8.7 | 4.4 | 11.8 | 4.9 |
| Median | 21.8 | | 8.3 | | 11.5 | |

TABLE 2

| | Change From Control | | |
|---|---|---|---|
| Sample | μM LPX + GPX | μM GPX | Calculated μM LPX |
| Control | n/a | n/a | n/a |
| 502 | −18.4 | −12.8 | −5.7 |
| 503 | −22.1 | −17.3 | −4.9 |
| 504 | −14.5 | −12.5 | −2.0 |
| 505 | −19.2 | −15.2 | −4.0 |
| 506 | −17.9 | −13.8 | −4.2 |
| 507 | −20.7 | −16.0 | −4.7 |
| 508 | −19.8 | −15.2 | −4.5 |
| 509 | −20.6 | −16.1 | −4.6 |
| 510 | −10.6 | −16.5 | 5.9 |
| 511 | −12.9 | −16.1 | 3.2 |
| 512 | −7.3 | −15.3 | 8.0 |
| 513 | −10.8 | −16.5 | 5.7 |
| 514 | −12.3 | −16.5 | 4.2 |
| 515 | −7.7 | −16.3 | 8.5 |
| 516 | −9.5 | −16.5 | 7.0 |
| 517 | −10.6 | −16.3 | 5.7 |
| 518 | −24.6 | −20.4 | −4.2 |
| 519 | −11.3 | −16.2 | 4.9 |
| 520 | −17.8 | −16.7 | −1.1 |
| 521 | −9.7 | −16.1 | 6.4 |
| 523 | −13.3 | −16.4 | 3.1 |
| 524 | −7.4 | −15.7 | 8.3 |
| 525 | −13.9 | −16.9 | 2.9 |
| 526 | −13.4 | −16.4 | 3.1 |
| 527 | −27.1 | −21.4 | −5.7 |
| 528 | −15.0 | −16.6 | 1.6 |
| 529 | −13.3 | −16.5 | 3.3 |
| 530 | −12.6 | −16.6 | 4.0 |
| 531 | −16.3 | −16.8 | 0.5 |
| 532 | −8.4 | −15.8 | 7.3 |
| 533 | −14.2 | −17.0 | 2.7 |
| 534 | −7.0 | −15.3 | 8.4 |
| 535 | −27.8 | −22.0 | −5.7 |
| 536 | −24.4 | −18.9 | −5.5 |
| 537 | −6.0 | −16.3 | 10.3 |
| 538 | −22.1 | −18.4 | −3.7 |
| 539 | −25.0 | −18.7 | −6.3 |
| 540 | −23.6 | −21.0 | −2.6 |
| 541 | −24.2 | −20.3 | −3.9 |
| 542 | −16.8 | −18.0 | 1.2 |
| 543 | −16.8 | −16.7 | −0.1 |
| 544 | −11.2 | −11.2 | 0.0 |
| 545 | −9.8 | −14.6 | 4.8 |
| 546 | −9.3 | −7.5 | −1.9 |
| 547 | −35.3 | −24.7 | −10.6 |
| 548 | −13.7 | −16.8 | 3.2 |
| 549 | −30.9 | −22.7 | −8.1 |
| 550 | −23.1 | −21.0 | −2.1 |
| 551 | 9.4 | 3.6 | 5.8 |
| 552 | −16.9 | −15.9 | −1.0 |
| 553 | −13.6 | −16.2 | 2.6 |
| 554 | −9.1 | −14.6 | 5.5 |
| 555 | −9.5 | −7.8 | −1.8 |
| 556 | −20.3 | −19.1 | −1.1 |
| 557 | −23.0 | −19.2 | −3.8 |
| 558 | −24.6 | −19.5 | −5.1 |

TABLE 2-continued

Change From Control

| Sample | µM LPX + GPX | µM GPX | Calculated µM LPX |
|---|---|---|---|
| 559 | −19.3 | −16.5 | −2.8 |
| 560 | −19.8 | −17.0 | −2.8 |
| 561 | −17.6 | −16.6 | −0.9 |
| 562 | −14.6 | −16.0 | 1.4 |
| 563 | −3.2 | −7.6 | 4.4 |
| 564 | −25.9 | −22.5 | −3.4 |
| 565 | −11.7 | −12.2 | 0.4 |
| 566 | −9.5 | −2.9 | −6.6 |
| 567 | −21.1 | −16.4 | −4.7 |
| Average | −15.8 | −16.1 | 0.2 |
| Median | −14.6 | −16.5 | −0.1 |

Example 2

Assay of Media Specimen from In vitro Fertilization Culture to Measure Lysophosphatidic Acid (LPA) and Glycerol-3-phosphate (G3P) By a Redox-Coupled Enzymatic Reaction IVF embryo conditioned culture media were obtained from freshly cultured human as described in Example #1.

Reagents

Lysophospholipase (LYPL) was purchased from Asahi Chemical (Tokyo, Japan). Glycerol-3-phosphate oxidase (GPO) was purchased from Toyobo (Osaka, Japan). 4-aminoantipyrine (AAP) was purchased from Sigma Chemical Co., St. Louis, Mo. Glycerol-3-phosphate dehydrogenase (GDH), peroxidase (POD) and beta-Nicotinamide-adenine dinucleotide (NADH) were purchased from Roche (Boehringer Mannheim, Indianapolis, Ill.). 3,5-Dichloro-2-hydroxybenzenesulfonic acid (HDCBS) was purchased from Biosynth (Naperville, Ill.). Amplex Red reagent (10-acetyl-3,7-dihydroxyphenoxazine) was purchased from Molecular Probes, Inc. (Eugene, Oreg.). All lipid or glycerophosphatidyl standards were purchased from Avanti Polar Lipids, Alabaster, Ala. or Sigma Chemical Co.

Enzyme Assay

Using a 96 well microtiter plate, 5 µl of each sample was aliquotted into pairs of wells. In some cases, samples were diluted 1:10 in 50 mM Tris, pH 8.0 prior to being assayed. To one well of each pair, the "LPA+G3P" well, 150 µl of reaction enzyme mix containing 0.05 units LYPL, 10 units of G3P oxidase (GPO), 4 units of G3P dehydrogenase (GDH) in 50 mM Tris (pH 8.0) was added. 150 µl of reaction enzyme mix containing 10 units of G3P oxidase (GPO), 4 units of G3P dehydrogenase (GDH) in 50 mM Tris (pH 8.0) was added to the other "background G3P" wells. To activate the G3P cycling reaction, 45 µl of 1.5 mM NADH in 50 mM Tris (pH 8.0) was added to each well. The wells were then incubated at 37° C. for 30 minutes. Glycerol-3-phosphate was produced as an intermediate by LYPL digestion of LPA. The G3P oxidase converts G3P to dihydroxyacetone phosphate and $H_2O_2$, and G3P dehydrogenase converts the dihydroxyacetone phosphate back into G3P. This reaction oxidizes NADH to NAD, and, as cycling continues, both $H_2O_2$ and NAD accumulate.

The total amount of G3P was determined by determining the accumulation of $H_2O_2$ fluorometrically by adding 50 µl of a solution containing 0.8 units horseradish peroxidase and 3.2 mM Amplex™ Red reagent (10-acetyl-3,7-dihydroxyphenoxazine) in 50 mM Tris 8.0 and measuring the fluorescence using 545 nm excitation and 590 nm emission. Optionally, the accumulation of $H_2O_2$ was also determined colorimetrically by adding 50 µl of a solution containing 0.5 units peroxidase, 0.5% HDCBS and 0.15% AAP in 50 mM Tris 8.0 to each well and recording the absorbance at 505 nm. Optionally, the total amount of G3P was determined by monitoring the oxidation of NADH (i.e. the reduction of absorbance at 340 nm after the cycling action compared to $A_{340}$ before cycling).

Numerical values of G3P concentrations were obtained from a standard curve constructed from known G3P amounts. A control culture media was included within each assay (i.e. each plate) that was measured at different dilutions. In some cases, this control media was used to correct for background variations between different experiments. When the colorimetric method was used, the plate was blanked at 505 nm prior to color development.

Using fluorometric detection, the dynamic range of detection was 0.01 to 10 µM G3P, and in some cases, the dynamic range extended up to 35 µM G3P. 64 embryo media samples and 1 control sample were analyzed. The results are shown in Tables 3 and 4. Values were obtained for LPA+G3P and G3P alone. The difference between these values was calculated as the apparent total LPA. Cultured media samples were generally lower in G3P than the control media. Cultured media samples were generally higher in LPA than the control media. However, 15 out of 64 samples contained lower LPA values than the control media. Generally, the changes in G3P were −0.30 µM to −0.52 µM, and the changes in LPA were −0.12 µM to +0.26 µM. The average and median values were as follows. Average and median values, in µM, for the samples were 0.487 and 0.479 (for LPA+G3P), 0.313 and 0.315 (for G3P), and 0.175 and 0.175 (for LPA) compared to average values for the control media of 0.879 (for LPA+G3P), 0.751 (for G3P), and 0.128 (for LPA). Average and median values, in µM, for changes during culture from control were −0.392 and −0.400 (for LPA+G3P), −0.438 and −0.437 (for G3P), and 0.047 and −0.047 (for LPA).

TABLE 3

| Sample | µM LPA + G3P | +/−SD | µM G3P | +/−SD | Calculated µM LPA |
|---|---|---|---|---|---|
| Control 502 | 0.879 | 0.066 | 0.751 | 0.052 | 0.128 |
| 503 | 0.519 | | 0.276 | | 0.243 |
| 504 | 0.469 | | 0.206 | | 0.263 |
| 505 | 0.749 | | 0.364 | | 0.385 |
| 506 | 0.748 | | 0.346 | | 0.402 |
| 507 | 0.743 | | 0.404 | | 0.339 |
| 508 | 0.670 | | 0.366 | | 0.304 |
| 509 | 0.620 | | 0.382 | | 0.238 |
| 510 | 0.541 | | 0.334 | | 0.207 |
| 511 | 0.548 | | 0.308 | | 0.240 |
| 512 | 0.585 | | 0.315 | | 0.270 |
| 513 | 0.562 | | 0.331 | | 0.231 |
| 514 | 0.612 | | 0.327 | | 0.285 |
| 515 | 0.484 | | 0.344 | | 0.140 |
| 516 | 0.556 | | 0.332 | | 0.224 |
| 517 | 0.546 | | 0.345 | | 0.201 |
| 518 | 0.458 | | 0.330 | | 0.128 |
| 519 | 0.509 | | 0.331 | | 0.178 |
| 520 | 0.503 | | 0.289 | | 0.214 |
| 521 | 0.458 | | 0.293 | | 0.165 |
| 523 | 0.471 | | 0.292 | | 0.179 |
| 524 | 0.514 | | 0.316 | | 0.198 |
| 525 | 0.513 | | 0.300 | | 0.213 |
| 526 | 0.452 | | 0.327 | | 0.125 |
| 527 | 0.451 | | 0.287 | | 0.164 |
| 528 | 0.471 | | 0.282 | | 0.189 |

TABLE 3-continued

| | | | |
|---|---|---|---|
| 529 | 0.461 | 0.308 | 0.153 |
| 530 | 0.524 | 0.324 | 0.200 |
| 531 | 0.460 | 0.233 | 0.227 |
| 532 | 0.435 | 0.269 | 0.166 |
| 533 | 0.475 | 0.312 | 0.163 |
| 534 | 0.555 | 0.344 | 0.211 |
| 535 | 0.476 | 0.345 | 0.131 |
| 536 | 0.561 | 0.359 | 0.202 |
| 537 | 0.404 | 0.291 | 0.113 |
| 538 | 0.491 | 0.295 | 0.196 |
| 539 | 0.512 | 0.343 | 0.169 |
| 540 | 0.478 | 0.327 | 0.151 |
| 541 | 0.510 | 0.339 | 0.171 |
| 542 | 0.546 | 0.322 | 0.224 |
| 543 | 0.507 | 0.324 | 0.183 |
| 544 | 0.389 | 0.257 | 0.132 |
| 545 | 0.453 | 0.450 | 0.003 |
| 546 | 0.515 | 0.309 | 0.206 |
| 547 | 0.545 | 0.317 | 0.228 |
| 548 | 0.480 | 0.289 | 0.191 |
| 549 | 0.486 | 0.370 | 0.116 |
| 550 | 0.507 | 0.352 | 0.155 |
| 551 | 0.295 | 0.236 | 0.059 |
| 552 | 0.347 | 0.253 | 0.094 |
| 553 | 0.306 | 0.234 | 0.072 |
| 554 | 0.400 | 0.264 | 0.136 |
| 555 | 0.375 | 0.272 | 0.103 |
| 556 | 0.474 | 0.296 | 0.178 |
| 557 | 0.420 | 0.284 | 0.136 |
| 558 | 0.496 | 0.292 | 0.204 |
| 559 | 0.344 | 0.296 | 0.048 |
| 560 | 0.289 | 0.278 | 0.011 |
| 561 | 0.348 | 0.287 | 0.061 |
| 562 | 0.430 | 0.310 | 0.120 |
| 563 | 0.357 | 0.265 | 0.092 |
| 564 | 0.477 | 0.319 | 0.158 |
| 565 | 0.470 | 0.342 | 0.128 |
| 566 | 0.436 | 0.365 | 0.071 |
| 567 | 0.397 | 0.314 | 0.083 |

| | LPX + GPX | +/−SD | GPX | +/−SD | LPX | +/−SD |
|---|---|---|---|---|---|---|
| Average | 0.487 | 0.096 | 0.313 | 0.042 | 0.175 | 0.078 |
| Median | 0.479 | | 0.315 | | 0.175 | |

TABLE 4

Change From Control

| Sample | μM LPA + G3P | μM G3P | Calculated μM LPA |
|---|---|---|---|
| Control | n/a | n/a | n/a |
| 503 | −0.360 | −0.475 | 0.115 |
| 504 | −0.410 | −0.545 | 0.135 |
| 505 | −0.130 | −0.387 | 0.257 |
| 506 | −0.131 | −0.405 | 0.274 |
| 507 | −0.136 | −0.347 | 0.211 |
| 508 | −0.209 | −0.385 | 0.176 |
| 509 | −0.259 | −0.369 | 0.110 |
| 510 | −0.338 | −0.417 | 0.079 |
| 511 | −0.331 | −0.443 | 0.112 |
| 512 | −0.294 | −0.436 | 0.142 |
| 513 | −0.317 | −0.420 | 0.103 |
| 514 | −0.267 | −0.424 | 0.157 |
| 515 | −0.395 | −0.407 | 0.012 |
| 516 | −0.323 | −0.419 | 0.096 |
| 517 | −0.333 | −0.406 | 0.073 |
| 518 | −0.421 | −0.421 | 0.000 |
| 519 | −0.370 | −0.420 | 0.050 |
| 520 | −0.376 | −0.462 | 0.086 |
| 521 | −0.421 | −0.458 | 0.037 |
| 523 | −0.408 | −0.459 | 0.051 |
| 524 | −0.365 | −0.435 | 0.070 |
| 525 | −0.366 | −0.451 | 0.085 |
| 526 | −0.427 | −0.424 | −0.003 |

TABLE 4-continued

Change From Control

| Sample | μM LPA + G3P | μM G3P | Calculated μM LPA |
|---|---|---|---|
| 527 | −0.428 | −0.464 | 0.036 |
| 528 | −0.408 | −0.469 | 0.061 |
| 529 | −0.418 | −0.443 | 0.025 |
| 530 | −0.355 | −0.427 | 0.072 |
| 531 | −0.419 | −0.518 | 0.099 |
| 532 | −0.444 | −0.482 | 0.038 |
| 533 | −0.404 | −0.439 | 0.035 |
| 534 | −0.324 | −0.407 | 0.083 |
| 535 | −0.403 | −0.406 | 0.003 |
| 536 | −0.318 | −0.392 | 0.074 |
| 537 | −0.475 | −0.460 | −0.015 |
| 538 | −0.388 | −0.456 | 0.068 |
| 539 | −0.367 | −0.408 | 0.041 |
| 540 | −0.401 | −0.424 | 0.023 |
| 541 | −0.369 | −0.412 | 0.043 |
| 542 | −0.333 | −0.429 | 0.096 |
| 543 | −0.372 | −0.427 | 0.055 |
| 544 | −0.490 | −0.494 | 0.004 |
| 545 | −0.426 | −0.301 | −0.125 |
| 546 | −0.364 | −0.442 | 0.078 |
| 547 | −0.334 | −0.434 | 0.100 |
| 548 | −0.399 | −0.462 | 0.063 |
| 549 | −0.393 | −0.381 | −0.012 |
| 550 | −0.372 | −0.399 | 0.027 |
| 551 | −0.584 | −0.515 | −0.069 |
| 552 | −0.532 | −0.498 | −0.034 |
| 553 | −0.573 | −0.517 | −0.056 |
| 554 | −0.479 | −0.487 | 0.008 |
| 555 | −0.504 | −0.479 | −0.025 |
| 556 | −0.405 | −0.455 | 0.050 |
| 557 | −0.459 | −0.467 | 0.008 |
| 558 | −0.383 | −0.459 | 0.076 |
| 559 | −0.535 | −0.455 | −0.080 |
| 560 | −0.590 | −0.473 | −0.117 |
| 561 | −0.531 | −0.464 | −0.067 |
| 562 | −0.449 | −0.441 | −0.008 |
| 563 | −0.522 | −0.486 | −0.036 |
| 564 | −0.402 | −0.432 | 0.030 |
| 565 | −0.409 | −0.409 | 0.000 |
| 566 | −0.443 | −0.386 | −0.057 |
| 567 | −0.482 | −0.437 | −0.045 |
| Average | −0.392 | −0.438 | 0.047 |
| Median | −0.400 | −0.437 | 0.047 |

Example 3

Liquid Chromatography-Mass Spectrometry Analysis of Bioactive Lipids in Embryo Culture Media IVF embryo conditioned culture media are obtained from freshly cultured human embryos as described in Example #1.

Reagents

Methanol, chloroform and hydrochloric acid, are purchased from Fisher Scientific. All lipid or glycerophosphatidyl standards are purchased from Avanti Polar Lipids, Alabaster, Ala. or Sigma Chemical Co. LC-MS-MS triple quadrapole instrument is a Quattro Ultima (MicroMass, Beverly Mass.). C18 columns are purchased from Keystone Scientific (Bellefonte, Pa.).

Sample Preparation

IVF media samples are diluted in methanol in preparation for analysis on the LC-MS. Samples are diluted 1:10 by combining 10 μl of each sample with 90 μl methanol. Samples are then centrifuged to remove precipitated protein and placed into maximum recovery autosampler vials. Alternatively, samples are extracted using methanol:chloroform (2:1), dried under nitrogen gas, and resuspended in methanol before being analyzed. Alternatively, samples are purified using solid phase extraction (SPE) such as reverse phase or anion exchange resins before being analyzed.

Liquid Chromatography-Mass Spectrometry

Sample separation and delivery to the mass spectrometer are performed using a Waters Alliance 2790 HPLC system (Waters, Milford, Mass.) with a C18 column (BetaBasic C18, 20×2 mm i.d., 5 μm particle size) obtained from Keystone Scientific (Bellefonte, Pa.). A gradient mobile phase is applied with solvent A containing methanol and solvent B containing water. In some cases, additives are included in solvent A and B to improve chromatography, such as sodium phosphate, formic acid, and ammonium acetate. Typically, chromatograms are about 16 minutes long with the following gradient conditions: Initial, 60% Solvent A, 40% Solvent B; 4 min: 60% Solvent A, 40% Solvent B; 16 min: 90% Solvent A, 10% Solvent B. The flow rate is maintained at 0.2 ml/min.

Bioactive lipids of interest are quantified using the Quattro Ultima Triple Quadrapole mass spectrometer equipped with an ESI source. Instrument settings and tuning parameters are optimized for each lipid using standard lipid reagents as controls. Using multiple reaction monitoring (MRM) mode for maximum sensitivity, specific parent-daughter pairs are measured for each lipid of interest. Specific lipids elute from the LC column and are introduced into the mass spec at different times during the analysis. Using this analysis, individual lipids or multiple lipids may be quantified during a single run.

Numerical values of specific lipid concentrations are obtained from standard curves constructed from known lipid amounts. A standard curve is analyzed for each separate lipid or class of lipid. In some cases, a known amount of an internal standard consisting of $C^{13}$-labelled lipid is included in each sample to correct for sample-to-sample variation. Alternatively, lipids that contain fatty acid chains that do not naturally exist in these samples, such as 17:0 fatty acid, may be used as internal standards.

What is claimed is:

1. A method for evaluating a biological characteristic in an in vitro fertilized embryo, comprising the steps of:
   (a) obtaining a media specimen from an in vitro culture containing the embryo;
   (b) measuring a concentration of one or more bioactive lipids in the media specimen;
   (c) comparing the concentration to a pre-determined level of the detected bioactive lipid; and
   (d) correlating the concentration to a biological characteristic in the embryo.

2. The method of claim 1 wherein the biological characteristic is the likelihood that an in vitro fertilized embryo will develop to term.

3. The method of claim 1 wherein the biological characteristic is the likelihood that an in vitro fertilized embryo will implant upon transfer into a uterus.

4. The method of claim 1 wherein the biological characteristic is the likelihood of a multiple pregnancy.

5. The method of claim 1 wherein the standard level is obtained by measuring the detected bioactive lipid in specimens of in vitro embryo culture media, collected under the substantially the same conditions, from embryos which exhibit a desirable biological characteristic, and calculating a mean of those levels.

6. The method of claim 1 wherein the standard level is obtained by measuring the detected bioactive lipid in specimens of in vitro embryo culture media, collected under the substantially the same conditions, from embryos which exhibit desirable biological characteristic, and calculating a median of those levels.

7. The method of claim 1 wherein the bioactive lipid is selected from the group consisting of lysophospholipids, glycerophosphatidyl compounds, sphingolipids, and combinations thereof.

8. The method of claim 7 wherein the bioactive lipid is at least one lysophospholipid with the general structure:

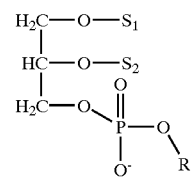

wherein R is selected from the group consisting of hydrogen, choline, inositol, ethanolamine, serine, and glycerol; $S_1$ is a single fatty acid chain linked by an acyl linkage, or a hydrogen; and $S_2$ is a single fatty acid linked by an acyl linkage if $S_1$ is a hydrogen, or a hydrogen if $S_1$ is a single fatty acid chain.

9. The method of claim 8 wherein R is hydrogen.

10. The method of claim 8 wherein R is choline.

11. The method of claim 8 wherein R is inositol.

12. The method of claim 8 wherein R is ethanolamine.

13. The method of claim 8 wherein R is glycerol.

14. The method of claim 8 wherein R is serine.

15. The method of claim 7 wherein the bioactive lipid is at least one lysophospholipid with the general structure:

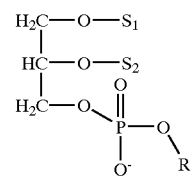

wherein R is selected from the group consisting of hydrogen, choline, inositol, ethanolamine, serine, and glycerol; $S_1$ is a single long chain alkyl or akenyl, or hydrogen; and $S_2$ is a single long chain alkyl or alkenyl if $S_1$ is hydrogen, or hydrogen if $S_1$ is a single long chain alkyl or akenyl.

16. The method of claim 15 wherein R is hydrogen.

17. The method of claim 15 wherein R is choline.

18. The method of claim 15 wherein R is inositol.

19. The method of claim 15 wherein R is ethanolamine.

20. The method of claim 15 wherein R is glycerol.

21. The method of claim 15 wherein R is serine.

22. The method of claim 7 wherein the bioactive lipid is at least one glycerophosphitidyl compound selected from the group consisting of: glycerol-3-phosphate, glycerophosphitidyl inositol, glycerophosphitidyl choline, glycerophosphitidyl serine, glycerophosphitidyl glycerol, glycerophosphitidyl ethanolamine, and combinations thereof.

23. The method of claim 7 wherein the bioactive lipid is at least one sphingolipid selected from the group consisting of: sphingosine-1-phosphate, sphinganine-1-phosphate, sphingomyelin, and combinations thereof.

24. The method of claim 7 wherein the bioactive lipid is at least one sphingolipid with the general formula:

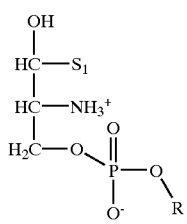

wherein $S_1$ is an alkyl or alkenyl chain of 15 carbons in length, and wherein R is selected from the group consisting of hydrogen, choline, inositol, ethanolamine, glycerol, and serine.

25. The method of claim 24 wherein $S_1$ a 15:1 alkenyl chain, and R is choline.

26. The method of claim 1 wherein the in vitro fertilized embryo is cocultured on a feeder cell line.

27. The method of claim 25 wherein the feeder cell line is of human origin.

28. The method of claim 25 wherein the feeder cell line is obtained from a patient who is to be the recipient the in vitro fertilized embryo.

29. The method of claim 25 wherein the feeder cell line is an endometrial epithelial cell line.

30. The method of claim 28 wherein the feeder cell line is an endometrial epithelial cell line.

31. The method of claim 1 wherein the media specimen is obtained from an in vitro culture whose embryo is between approximately one hour and approximately twenty days old.

32. The method of claim 1 wherein the embryo is between approximately one day and approximately ten days old.

33. The method of claim 1 wherein the embryo is approximately 2 days old.

34. The method of claim 1 wherein the step of measuring one or more bioactive lipids is accomplished by mass spectroscopy.

35. The method of claim 1 wherein the step of measuring one or more bioactive lipids is accomplished by an enzymatic chemical reaction.

36. The method of claim 35 wherein the enzymatic chemical reaction is a cycling reaction.

37. The method of claim 35 wherein the enzymatic chemical reaction comprises the use of at least one enzyme selected from the group consisting of lysophospholipase, a glycerophosphatidyl compound phosphodiesterase, glycerol-3-phosphate dehydrogenase, and glycerol-3-phosphate oxidase.

38. The method of claim 35 wherein the enzymatic chemical reaction comprises:
   i) converting lysophospholipids in the specimen into glycero-3-phosphate by incubating with lysophospholipase and a glycerophosphatidyl compound phosphodiesterase; and
   ii) determining the total concentration of G3P using an enzymatic cycling reaction.

39. A method for evaluating a biological characteristic in an in vitro fertilized embryo, comprising the steps of:
   (a) obtaining a media specimen from an in vitro culture containing the embryo at two or more time intervals;
   (b) measuring the combination of one or more bioactive lipids in each of the media specimens,
   (c) calculating the change in level of the bioactive lipids in the media specimen over the two or more time intervals; and
   (d) correlating the change obtained in step (c) to a biological characteristic of the embryo.

40. A pre-packaged analytic kit for measuring levels of at least one glycerophosphatidyl compounds in media specimen from an in vitro fertilized embryo culture comprising:
   a glycerophosphatidyl compound phosphodiesterase;
   glycerol-3-phosphate oxidase;
   glycerol-3-phosphate dehydrogenase; and
   instructions for carrying out the analysis,
   wherein the components of the kit are packaged together in a container.

41. The pre-packaged diagnostic kit of claim 40, further comprising a glycerophosphatidyl compound standard.

42. A pre-packaged analytic kit for measuring levels of at least one lysophospholipid in a media specimen from an in vitro fertilized embryo culture comprising:
   a lysophospholipase;
   a glycerophosphatidyl compound phosphodiesterase;
   a glycerol-3-phosphate dehydrogenase;
   a glycerol-3-phosphate oxidase; and
   instructions for carrying out the analysis,
   wherein the components of the kit are packaged together in a container.

43. The pre-packaged diagnostic kit of claim 40 further comprising a lysophospholipid standard.

44. A pre-packaged analytic kit for measuring levels of glycerophosphatidyl choline in a media specimen from an in vitro fertilized embryo culture comprising:
   a glycerophosphatidylcholine phosphodiesterase;
   choline oxidase;
   peroxidase; and
   instructions for carrying out the analysis,
   wherein the components of the kit are packaged together in a container.

45. The pre-packaged diagnostic kit of claim 44, further comprising a glycerophosphatidylcholine standard.

* * * * *